(12) United States Patent
Sims et al.

(10) Patent No.: US 6,309,444 B1
(45) Date of Patent: Oct. 30, 2001

(54) POST-BLENDING VALVE DEGASSER

(75) Inventors: Carl W. Sims, St. Paul; Yuri Gerner, Mendota Heights; Thomas J. Thielen, Plymouth, all of MN (US)

(73) Assignee: Systec Inc., New Brighton, MN (US)

( * ) Notice: Subject to any disclaimer, the term of this patent is extended or adjusted under 35 U.S.C. 154(b) by 0 days.

(21) Appl. No.: 09/635,049

(22) Filed: Aug. 8, 2000

Related U.S. Application Data

(63) Continuation-in-part of application No. 09/378,592, filed on Aug. 20, 1999, now Pat. No. 6,248,157.

(51) Int. Cl.[7] .............................. B01D 19/00; B01D 15/08
(52) U.S. Cl. ............................. 95/46; 96/6; 96/8; 96/10; 210/198.2
(58) Field of Search ................... 95/46; 96/6, 8, 96/10; 210/198.2

(56) References Cited

U.S. PATENT DOCUMENTS

| | | | |
|---|---|---|---|
| 3,463,615 | * 8/1969 | Sochor | 95/46 X |
| 3,668,837 | 6/1972 | Gross . | |
| 4,004,587 | * 1/1977 | Jess | 96/6 |
| 4,133,767 | 1/1979 | Bakalyar et al. . | |
| 4,430,098 | 2/1984 | Bowman et al. . | |
| 4,886,528 | * 12/1989 | Aaltonen et al. | 96/6 |
| 4,985,055 | * 1/1991 | Thorne et al. | 96/6 |
| 4,986,827 | * 1/1991 | Shibata | 96/6 |
| 4,994,180 | 2/1991 | Sims et al. . | |
| 4,997,464 | * 3/1991 | Kopf | 96/6 |
| 5,183,486 | 2/1993 | Gatten et al. . | |
| 5,340,384 | 8/1994 | Sims . | |
| 5,425,803 | * 6/1995 | Van Schravendijk et al. | 95/46 |
| 5,522,917 | * 6/1996 | Honda et al. | 96/6 X |
| 5,743,941 | * 4/1998 | Gerner et al. | 96/10 |
| 5,762,684 | * 6/1998 | Hayashi et al. | 95/46 X |
| 5,980,742 | * 11/1999 | Saitoh | 95/46 X |
| 6,042,634 | * 3/2000 | Van Tassel et al. | 96/10 X |

FOREIGN PATENT DOCUMENTS

| | | | |
|---|---|---|---|
| 05-184812 | * 1/1989 | (JP) | 96/6 |
| 3822093 | * 1/1989 | (DE) | 95/46 |
| 01-215312 | * 8/1989 | (JP) | 95/46 |
| 02-290201 | * 11/1990 | (JP) | 95/46 |

* cited by examiner

*Primary Examiner*—Robert H. Spitzer
(74) *Attorney, Agent, or Firm*—Haugen Law Firm PLLP

(57) ABSTRACT

A flow-through vacuum degassing unit for degassing a mobile phase includes a vacuum conduit adapted to be connected to a source for creating a vacuum in the conduit, an inlet port and an outlet port for admitting and discharging the mobile phase to be degassed, a degassing tube for conducting the mobile phase through the conduit, wherein the degassing tube is a gas-permeable, liquid impermeable material. In a particular embodiment, the degassing tube receives multiple mobile phases blended together in a discrete volume of desired composition.

18 Claims, 8 Drawing Sheets

302

POST-BLENDING VALVE DEGASSER

CROSS-REFERENCE TO RELATED APPLICATIONS

The present application is a Continuation-in-Part of application Ser. No. 09/378,592, filed Aug. 20, 1999, entitled "VACUUM DEGASSING", herein incorporated by reference, now U.S. Pat. No. 6,248,157.

FIELD OF THE INVENTION

The present invention relates to vacuum degassing systems generally, and more particularly to systems for degassing mobile phase materials in chromatographic applications. This invention also relates to methods for degassing mobile phase materials.

BACKGROUND OF THE INVENTION

There are many chemical applications, particularly analytical applications, involving the use of liquid solvents, reactants, or the like wherein the presence of dissolved gases, particularly air, is undesirable. An example of such an application relates to the mobile phase in high performance liquid chromatography where the presence of even small amounts of dissolved gases, and in particular oxygen, interferes with the accuracy and sensitivity of the results obtained. For example, air dissolved in the mobile phase can manifest itself in the form of bubbles, with the bubbles causing measurement noise and drift as the mobile phase passes through a detector. If the dissolved species be chemically active, as in the case of oxygen in air, unwanted changes or deterioration in the mobile phase can occur. Indeed, the detrimental effect of the dissolved species is related to the relative concentration of the species in the mobile phase. These undesirable species are typically removed by a known degassing process. It correspondingly follows that the more efficient the removal or degassing system is, the more accurate and desirable the system is.

Liquid degassing is necessary to many processes and, consequently, has long been actively pursued. Techniques for liquid degassing have included operations such as heating or boiling of the liquid to be degassed, exposing the material to a reduced pressure environment or vacuum, and use of combinations of heat and vacuum to reduce the amount of dissolved gases in the liquid. Exposure to ultrasonic energy has also been employed. As conventionally applied, however, these traditional techniques have generally fallen short of the desired degree of separation efficiency.

An additional means of degassing liquid involving the passing of a fine stream of bubbles of inert gas such as helium through the solution to be degassed is shown by Bakalyar et al (U.S. Pat. No. 4,133,767), and in apparatus such as is disclosed in Sims et al (U.S. Pat. No. 4,994,180) which was coinvented by the co-inventor in the present application and assigned to the same assignee as in the present invention.

Vacuum degassing through a membrane apparatus has long been known, and generally utilizes a length of relatively small diameter, thin-walled semi-permeable synthetic polymer resin material contained within an enclosed chamber and held under a reduced pressure or vacuum. To perform the degassing, the liquid to be degassed is caused to flow through the chamber. One such apparatus is shown by Sims (U.S. Pat. No. 5,340,384), which was co-invented by the co-inventor in the present application and assigned to the same assignee as in the present invention. Other such devices are shown in U.S. Pat. Nos. 5,183,486, 4,430,098, and 3,668,837.

While each of these devices employ a flow-through tube vacuum degassing approach, there remains a need, particularly with devices associated with high performance liquid chromatography (HPLC) instruments, to make degassing of liquids, and in particular the mobile phase, more efficient. One particular limitation or drawback associated with known devices concerns the efficiency of the degassification operation with respect to the composition of the tubing itself. Materials presently used in degassing applications include PTFE, PFA, and silicone rubber. Such materials, while generally suitable for degassing applications, require that tube wall thicknesses be as thin as possible due to the relatively low gas permeability of such materials.

Amorphous perfluorinated copolymers reportedly have substantially higher permeabilities for certain gases than the corresponding permeabilities of PTFE. The present inventors have found that by using amorphous perfluorinated copolymers, such as those marketed by Du Pont under the tradename Teflon AF, in a tubular configuration, increased permeability over similar PTFE tubing is achieved. Thus, greater gas mass transfer rates may be obtained through degassing tubes fabricated from Teflon AF such that Teflon AF degassing tubes may be fabricated with increased wall thicknesses while retaining desired degassing capabilities. Increased tube wall thicknesses permit the undertaking of applications requiring higher pressures.

Because of the enhanced gas permeability property of materials utilized in accordance with the present invention, the diffusion rate of atmospheric gases from the mobile phase being degassed through the tubing wall is significantly increased. It appears likely that the increased gas permeability enhances the function of free (void) volume in the polymer component.

Known degassing systems typically perform the degassing function on the mobile phases prior to the point where mobile phases enter a proportioning valve, where the mobile phases are proportioned into discrete volumes (slugs) for processing through the HPLC apparatus. Generally, each mobile phase is degassed while flowing through long tubes that connect each mobile phase source to the proportioning valve apparatus. Because of the low permeability of the materials commonly utilized in the degassing tubes, each degassing tube must be quite long to provide the necessary mobile phase residence time in the degassing tube to allow the entrained gas to escape from the mobile phase.

Such a method of degassing the mobile phases presents several disadvantages. The cumulative size of the degassing tubes limits the location of such tubes within the HPLC apparatus, and results in a relatively large space or volume being required to house the degassing system. Additionally, known degassing methods position the degassing tubes upstream from the proportioning valve apparatus due to the length of tubing required to sufficiently degas the mobile phase. In HPLC systems where multiple mobile phases are utilized simultaneously, the mobile phases are mixed into one stream in the proportioning valve apparatus. Even if the mobile phases being received in the proportioning valve apparatus are properly degassed, subsequent mixing may result in formation of gas bubbles in the mixed or blended mobile phase stream. Thus, degassing downstream from the proportioning valve apparatus (post-blending) is desired.

Accordingly, it is a principal object of the present invention to provide a more efficient flow-through vacuum degassing system using one or more tubes formed from an amorphous perfluorinated copolymer.

A further object of the present invention is to reduce the required inside diameter and length of the degassing tube.

A still further object of the present invention is the provision of a degassing tube having a single lumen.

A yet further object of the present invention is the provision of a degassing tube having multiple lumen.

Another object of the present invention is to provide a means for interconnecting liquid chromatography instrument components which interconnecting means simultaneously degases the mobile phase while in transit between the components.

A still further object of the present invention is the provision of a degassing tube which has an increased wall thickness while maintaining a desired level of permissivity, thereby allowing the degassing tube to withstand higher vacuum environments.

A yet further object of the present invention is to efficiently degas the mobile phase in a liquid chromatography system after multiple mobile phase streams have been blended and proportioned into an individual mobile phase stream.

A still further object of the present invention is to efficiently degas the mobile phase for delivery to a liquid chromatographic auto sampler.

SUMMARY OF THE INVENTION

By means of the present invention, the efficiency of a flow-through vacuum degassing system utilizing an elongated gas-permeable tube is improved by reducing the required inside diameter and length of the tube. This is achieved by forming the tube from an amorphous perfluorinated copolymer such as Teflon AF. Amorphous perfluorinated copolymers have been reported to have permeabilities of up to two or three orders of magnitude greater than other semi-permeable polymeric resins typically utilized in degassing applications. By using such copolymers, it has been found that it is possible to significantly reduce the length of tubing utilized, which correspondingly and proportionally reduces the internal volume, improves the speed of response of the degassing channel to flow rate changes, and reduces startup time to reach equilibrium flow conditions. These improvements are achieved without either reduction or compromise in degassing performance.

One embodiment of the flow-through vacuum degassing system includes a conduit adapted to be connected to a source for creating a vacuum in the conduit, an inlet connection and an outlet connection for receiving and discharging a fluid to be degassed, and a gas-permeable, liquid-impermeable tube for conducting the fluid through the conduit, the tube being connected between the inlet connection and the outlet connection, the tube providing a means for fluidly interconnecting components in a liquid chromatography system. The tube may be fabricated from an amorphous perfluorinated copolymer, and may include one or more lumens.

Another embodiment of the flow-through vacuum degassing apparatus is adapted for degassing a blend of multiple liquids such that the blend may be employed directly as a degassed mobile phase in a liquid chromatography system.

An additional embodiment of the flow-through vacuum degassing apparatus is adapted to degas a liquid or a blend of multiple liquids to be used as a mobile phase fed to an HPLC auto sampler.

The present invention also contemplates a method of degassing one or more liquids in a flow-through vacuum apparatus. The method includes providing one or more mobile phases for transport in a gas-permeable, liquid-impermeable degassing tube wherein the tube is at least partially disposed in a sealed conduit, forming a chamber. The sealed conduit or chamber is adapted to be connected to a vacuum source for creating a vacuum within the chamber. The method further includes providing a means for drawing the mobile phases through the degassing tube. The degassing tube utilized in this method may be an amorphous perfluorinated copolymer.

DETAILED DESCRIPTION OF THE PREFERRED EMBODIMENTS

The objects and advantages enumerated above together with other objects, features and advances represented by the present invention will now be presented in terms of detailed embodiments described with reference to the attached drawing figures which are intended to be but one representative embodiment of various possible configurations of the invention. Other embodiments and aspects of the invention are recognized as being within the grasp of those having ordinary skill in the art.

Figure 1:
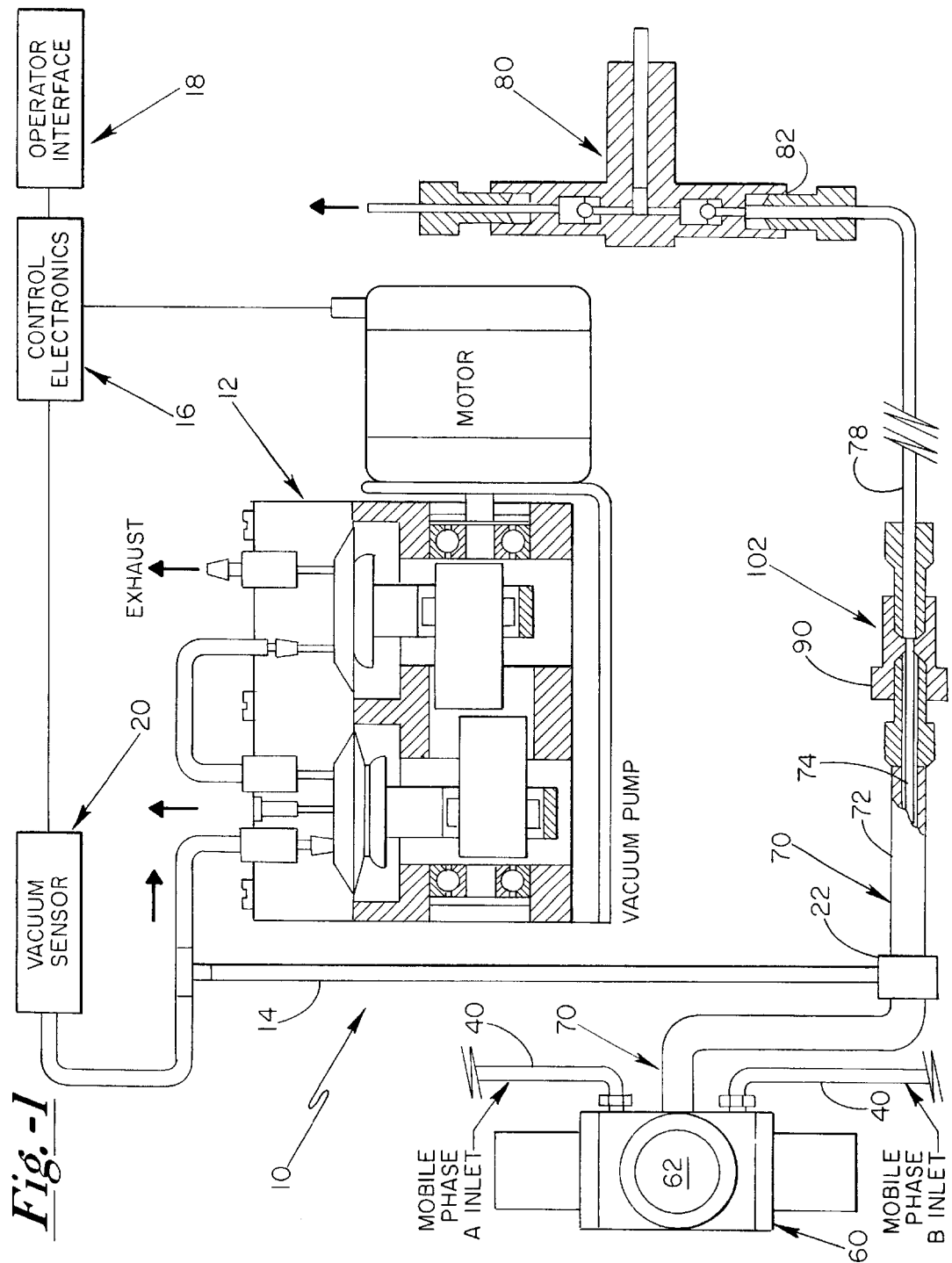
FIG. 1 is a schematic diagram showing the components of the present invention.

Referring now by characters of reference to the drawings, and first to FIG. 1, a combination mobile phase blending/vacuum degassing system 10 is shown. Although applicable to other systems, blending/degassing system 10 is preferably for use in a high performance liquid chromatography apparatus. Blending/degassing system 10 includes a vacuum pump 12 and a vacuum sensor 20 operably coupled to a hollow vacuum tube 14, an electronic control means 16 operably coupled to vacuum pump 12 and to vacuum sensor 20, and an operator interface 18 operably coupled to control means 16.

The details of vacuum pump 12 are described in application Ser. No. 09/378,592 filed Aug. 20, 1999, now U.S. Pat. No. 6,248,157, which patent is herein incorporated in its entirety.

Blending/degassing system 10 further includes mobile phase inlets 40, a blending chamber 60, a mobile phase degassing channel 70, a mobile phase transfer conduit 78 and a mobile phase pump 80. Blending chamber 60 is operably coupled to mobile phase inlets 40 and mobile phase degassing channel 70. Degassing channel 70 may also be operably coupled to transfer conduit 78, which transfer conduit 78 is operably coupled to mobile phase pump 80. In other embodiments, however, degassing channel 70 may be directly operably coupled to mobile phase pump 80 without utilizing an intermediate transfer conduit 78.

Vacuum tube 14 is connected to degassing channel 70 via a vacuum adapter 22, which vacuum adapter 22 provides a passageway through an outer surface 72 of degassing channel 70. Thus, a continuous enclosed passage is formed from within outer surface 72 into vacuum tube 14 through vacuum adapter 22.

The inlet flow paths for the multiple mobile phases are shown in FIG. 1 entering blending chamber 60. Blending chamber 60 preferably receives multiple mobile phase streams, though a single mobile phase stream inlet is also contemplated in the present invention. Each mobile phase stream preferably flows from an individual mobile phase reservoir such that each mobile phase stream is comprised of a single mobile phase.

A proportional valve 62 is contained within blending chamber 60 for combining individual inlet mobile phases into discrete volumes of blended mobile phase. In preferred embodiments, a low-pressure proportional valve is utilized for high-performance liquid chromatography (HPLC) applications. Proportional valve 62 programmably meters a desired volume of mobile phase from one or more of the mobile phase inlets 40 to provide a discrete known volume of mobile phase. The discrete mobile phase volume may comprise one or more mobile phase species.

Once the mobile phases have been blended into a discrete volume, the blended mobile phase is drawn into one or more degassing tubes 74 by the negative pressure created at the inlet side of mobile phase pump 80. Mobile phase pump 80 causes the blended mobile phase to flow through degassing tubes 74 and transfer conduit 78 to pump inlet 82. At least a portion of degassing tubes 74 is enclosed by degassing channel 70. As shown in FIG. 1, degassing channel 70 is coupled to transfer conduit 78 via a coupling union 90 such that the mobile phase is transferred from degassing tubes 74 to transfer conduit 78 through coupling union 90. As is shown more clearly in FIG. 2, a transfer duct 130 operably connects degassing tubes 74 with transfer channel 78 within coupling union 90.

Figure 2:
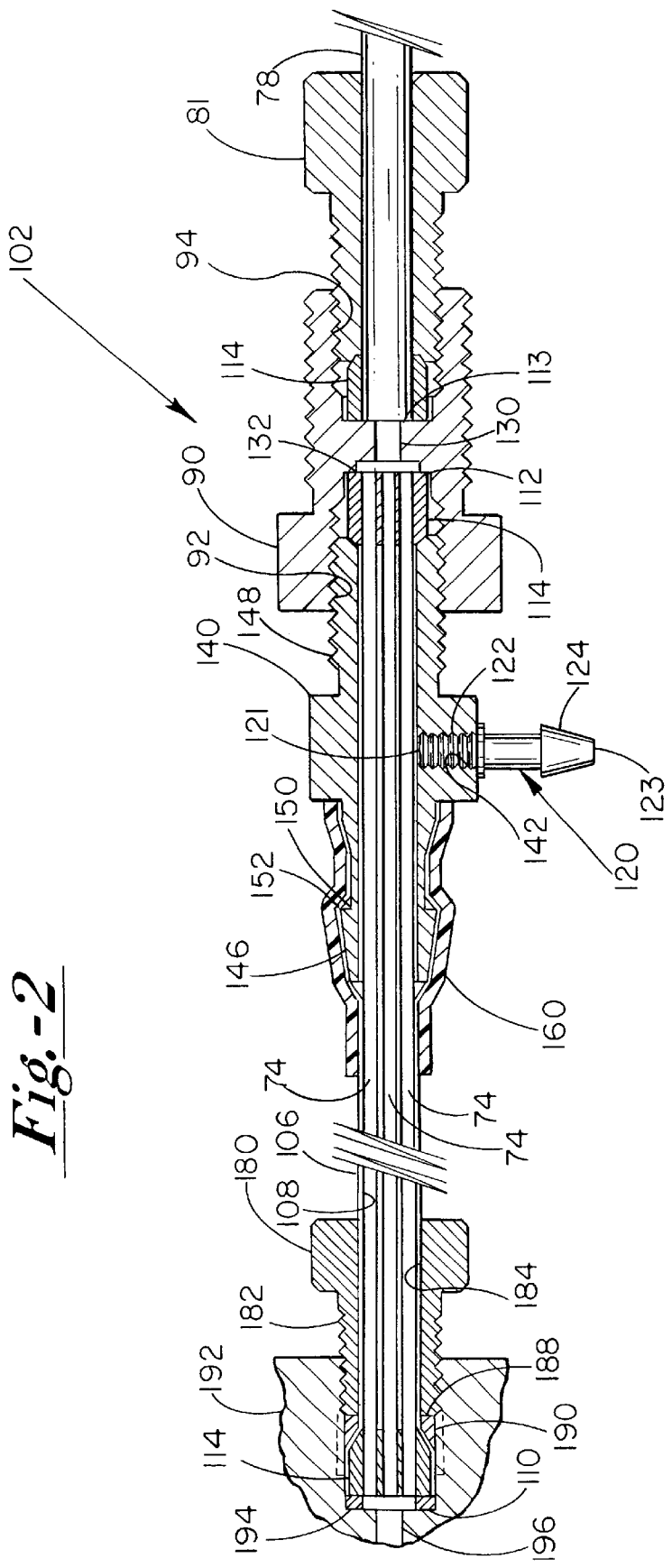
FIG. 2 is a cross-sectional view of a degassing tube assembly in accordance with the present invention.

FIG. 2 illustrates a portion of the blending/degassing system 10 of FIG. 1 in greater detail, in particular a degassing tube assembly 102 in accordance with one embodiment of the present invention. In the embodiment shown in FIG. 2, degassing tube assembly 102 includes multiple elongate gas-permeable degassing tubes 74 enclosed within an outer jacket 106. Outer jacket 106 is substantially tubular in shape, and is preferably fabricated from a heat-shrinkable FEP, PFA, or TEFZEL of shrink ratio 1.3 or 1.6. Other polymeric materials may be used which are sufficiently inert to withstand the environment within an HPLC system, and have sufficient wall strength to withstand an absolute vacuum environment within the jacket. Outer jacket 106 may be additionally supported internally or externally by a spiral spring or wrapping (not shown), which support prevents "kinking" when bending the degassing tube assembly 102 to fit within an HPLC system.

Degassing tubes 74 are preferably an amorphous perfluorinated copolymer, more preferably Teflon AF, and most preferably Teflon AF 2400, and may be adapted for use in transporting and degassing the mobile phase in a liquid chromatography application. Entrained or dissolved gas, particularly oxygen, in the mobile phase may escape through the gas-permeable sidewalls of tubes 74 while the mobile phase is transported and contained within the degassing tubes.

An enclosed interior portion 108 of degassing channel 70 is formed between ends 110, 112, thereby creating an enclosed chamber opening only to vacuum adapter 120. Compressible ferrules 114 are positioned within degassing channel 70 at ends 110, 112, and are appropriately bored to receive degassing tubes 74. The ferrules 114 are preferably sized and configured to effectively seal the interior portion 108 of degassing channel 70 at ends 110, 112, while allowing degassing tubes 74 to pass through to transfer duct 130. Ferrules 114 are preferably fabricated from a material which is inert to HPLC solvents, most preferably TEFZEL. Examples of other materials that may be used in place of TEFZEL are PFA, FEP, PTFE, and Kel-F.

Vacuum adapter 120 is provided for communication between interior portion 108 of degassing channel 70 and a vacuum source to evacuate the interior portion 108 and thereby remove gas that has permeated through degassing tubes 74. Such evacuation of the interior portion 108 of degassing channel 70 in fact drives the described degassing, as governed by Henry's Law of partial pressure, by drawing the gas from a relatively higher partial pressure to a relatively lower partial pressure. Such evacuation also assists in inhibiting "regassing" of the mobile phase. Regassing of the mobile phase can occur when gas that has permeated out from the mobile phase re-enters the mobile phase through the degassing tubes 74. By removing the permeated gas from around the degassing tubes 74, such regassing can be reduced or eliminated.

Vacuum adapter 120 is preferably a non-resilient, durable material, most preferably stainless steel. As is shown in FIG. 2, vacuum adapter 120 may include a threaded portion 122 and a nozzle portion 124 distal from the threaded portion 122. To effect the evacuation described above, vacuum adapter should be hollow so as to form a continuous passageway throughout its length, as from a threaded end 121 to a nozzle end 123. Threaded portion 122 of vacuum adapter 120 may be received by a threaded hole 142 in a sealing nut 140. When vacuum adapter 120 is in place in sealing nut 140, nozzle portion 124 of vacuum adapter 120 extends outwardly from the sealing nut. The threaded hole 142 in sealing nut 140 preferably forms a continuous passageway from interior portion 108 to the exterior of sealing nut 140. Thus, threaded portion 122 of vacuum adapter 120 may be inserted into threaded hole 142 to thereby provide a continuous passageway from interior portion 108 to nozzle end 123 of vacuum adapter 120. Threaded hole 142 is preferably sized to receive threaded portion 122 vacuum adapter 120 such that a gas-tight seal is formed between the vacuum adapter 120 and the sealing nut 140.

In other embodiments of the present invention, vacuum adapter 120 may be press-fit or friction fit in sealing nut 140. Other methods of securing vacuum adapter within sealing nut 140 are also contemplated in the present invention, so long as a continuous passageway is provided between interior portion 108 of and the vacuum tube 14, and a gas-tight seal is formed between the vacuum adapter 120 and the sealing nut.

Nozzle end 123 of vacuum adapter 120 is preferably positioned within vacuum line 14 such that permeated gas within interior portion 108 may be evacuated through vacuum adapter 120 and into vacuum tube 14 for removal through vacuum pump 12. Vacuum tube 14 may be constructed of any material appropriate for transporting gases in a near or absolute vacuum environment. Preferable materials are sufficiently rigid to maintain a substantially tubular configuration while the tube interior is under an absolute vacuum. The inner diameter of vacuum tube 14 should be sized to fit tightly around perimeter of vacuum adapter nozzle 124 such that a seal between the vacuum tube 14 and nozzle 124 is formed.

Sealing nut 140 is positioned between a portion of outer jacket 106 and degassing tubes 74 such that at least a portion of outer surface 146 of sealing nut 140 is in intimate contact with outer jacket 106. In a preferred embodiment, outer surface 146 of sealing nut 140 includes a threaded portion 148, which threaded portion 148 may be cooperatively received in a first threaded chamber 92 of coupling union 90 to compress ferrule 114 against end 112. Such compression forms a gas-tight seal between ferrule 114 and sealing nut 140, as well as between individual degassing tubes 74, to form a sealed end of degassing channel 70. The compressed ferrule 114, however, is configured to allow degassing tubes 74 to pass through the ferrule so as to transmit the mobile phase to transfer duct 130.

Outer surface 146 of sealing nut 140 may also include a barbed portion 150 in intimate contact with outer jacket 106. Barbed portion 150 of sealing nut 140 supports outer jacket 106 and a sealing tube 160. Sealing nut 140 is preferably a rigid material having high strength characteristics, most preferably stainless steel. Other materials that may be used in place of stainless steel include Titanium, PEEK, or Polyphenylene sulfide.

Sealing tube 160 generally comprises a short length of tubing which is fit over a portion of outer jacket 106 to force the outer jacket against barb portion 150 of sealing nut 140. Sealing tube 160 is sized and configured to fit over outer jacket 106 such that a vacuum seal is formed between the outer jacket and sealing nut 140. Barbed portion 150 of sealing nut 140 includes a relatively sharp ring 152 extending radially outwardly from sealing nut 140. Ring 152 provides a locus for effective sealing between sealing tube 160 and sealing nut 140 by causing outer jacket 106 to crimp around ring 152 when the sealing tube forces outer jacket against barbed portion 150. Various materials may be used in the manufacture of the sealing tube 160, but the material utilized must not cold flow, nor its compressive nature change in the presence of solvents or solvent vapors. Sealing tube 160 is preferably polyethylene, but materials such as TEFZEL, FEP, and PFA are examples of suitable alternatives.

Coupling union 90 includes a first interior threaded chamber 92, a second interior threaded chamber 94, and a transfer duct 130 connecting threaded chambers 92, 94. As described above, first threaded chamber 92 is sized and configured to receive threaded portion 148 of sealing nut 140. Degassing channel 70 is received into threaded chamber 92 until the degassing channel seats against end 112 of threaded chamber 92. Degassing tubes 74 within degassing channel 70 extend to a machined recess 132 adjacent threaded chamber end 112. Recess 132 allows mobile phase exiting degassing tubes 74 to efficiently flow into transfer duct 130. Second threaded chamber 94 is sized and configured to receive transfer conduit nut 81, which conduit nut 81 contains transfer conduit 78. Coupling union 90 may be manufactured from any material appropriate to an HPLC solvent environment, such as stainless steel, PEEK, Kel-F, polyphenylene sulfide, or other inert materials of sufficient strength. In some embodiments of the present invention, the coupling union end distal from the degassing channel may be configured to mate directly to an inlet of a mobile phase pump, as in pump inlet 82 shown in FIG. 1.

Transfer conduit 78 preferably connects degassing tube assembly 102 to mobile phase pump 80. Transfer conduit 78 is secured within transfer conduit nut 81 via a sealing ferrule 114. Transfer conduit nut 81 forces ferrule 114 against transfer conduit 78 and second threaded chamber end 113 to thereby seal transfer conduit 78 within conduit nut 81 and coupling union 90. In a preferred embodiment, transfer conduit 78 is abutted against transfer duct 130 so as to provide a continuous channel in which the mobile phase may flow. Transfer conduit 78 is preferably FEP, PFA, or PTFE, although other similar materials may be utilized.

Degassing tube assembly 102 further includes a proportioning valve nut 180 having an exterior threaded portion 182, and an interior hollow channel 184. Interior channel 184 is sized and configured to receive degassing channel 70 such that outer jacket 106 is in intimate contact with wall of hollow channel 184. In some embodiments of the present invention, exterior threaded portion 182 engages a female receptacle 190 in a proportioning valve housing 192. Preferably, at least a portion of female receptacle 190 is threaded to receive threaded portion 182 of valve nut 180. Proportioning valve nut 180 is preferably 316 stainless steel, but may be any material suitably inert to solvents and sufficiently strong to serve as a threaded nut. Examples of other materials that may be utilized in fabricating valve nut 180 are Polypropylene, PEEK, or polyphenylene Sulfide.

As proportioning valve nut 180 is inserted into female receptacle 190, valve nut 180 presses a compression ring 188 against outer jacket 106. The force on compression ring 188 is transferred to outer jacket 106, which in turn is forced against a ferrule 114. The force of the outer jacket 106 against the ferrule 114 results in a seal being formed between the outer jacket and the ferrule, thereby creating a sealed end to the interior portion 108 of degassing channel 70.

When fully inserted, degassing channel 70 abuts a spacer ring 194, which spacer ring 194 is adjacent female receptacle end 110. The spacer ring 194 provides a compressible landing zone for degassing tube 70 to press against, and also provides a space between the incoming mobile phase tube 196 and the inlets to the degassing tubes 74 so that mobile phase may be equally distributed among the degassing tubes 74. Spacer ring 194 is preferably PTFE, although other suitable materials may be used instead.

Figure 3:
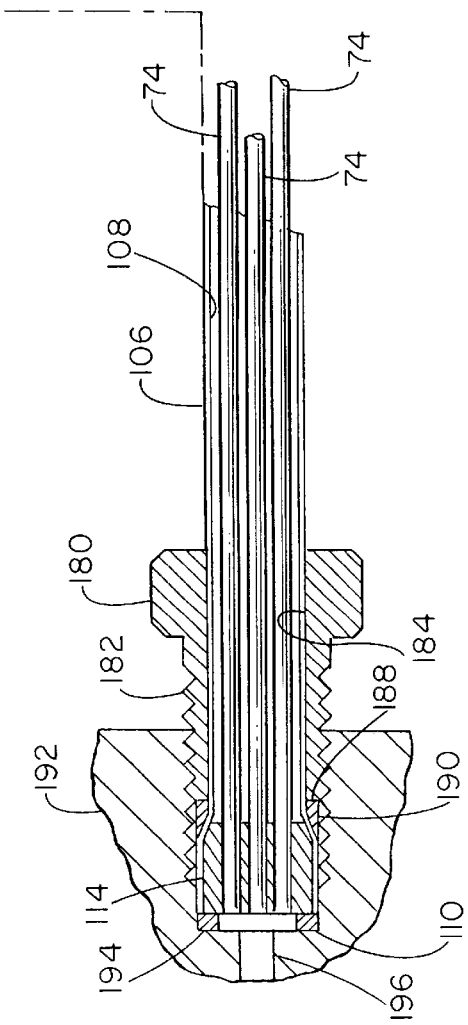
FIG. 3 is an enlarged view of the assembly shown in FIG. 2.

FIG. 3 is an enlarged view of the embodiment illustrated in FIG. 2. Like reference numerals have been used to indicate like subject matter between FIG. 2 and FIG. 3.

Figure 4:
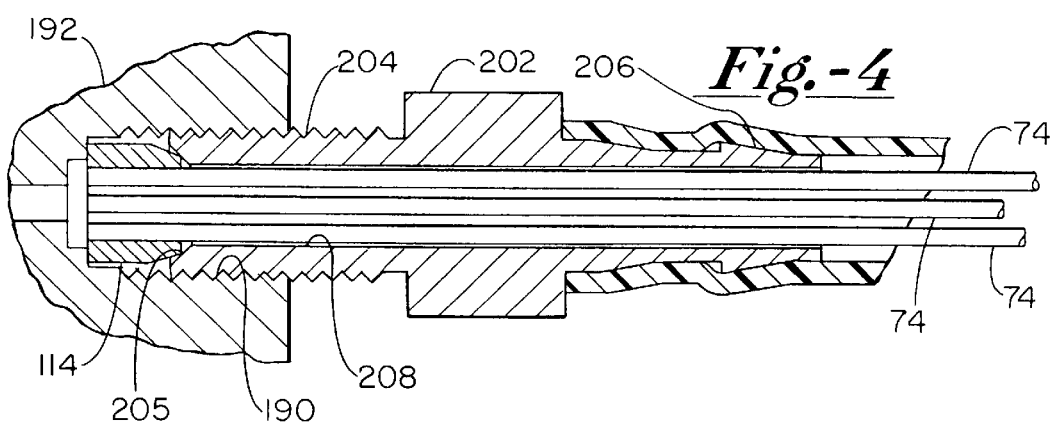
FIG. 4 is a cross-sectional view of an alternative embodiment of the proportioning valve body/proportioning valve nut interface.
Figure 5:
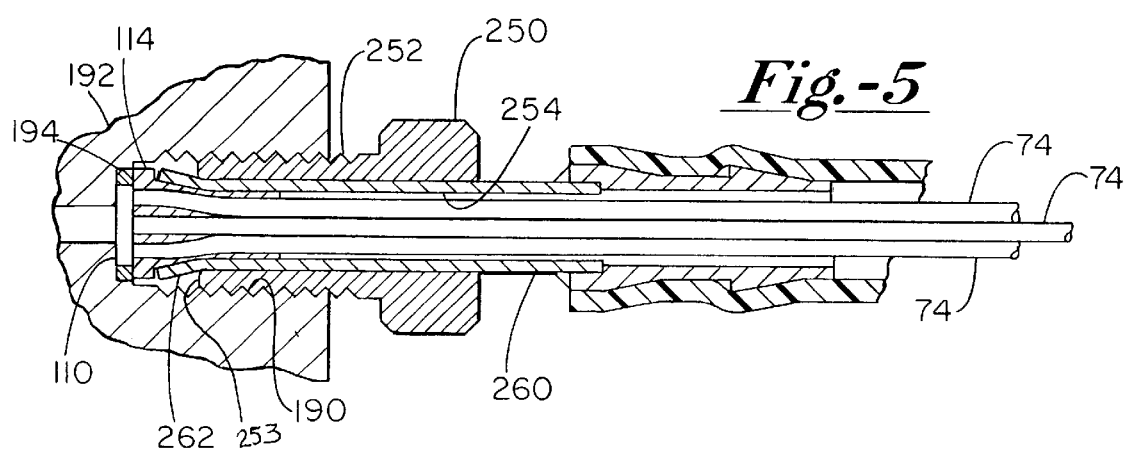
FIG. 5 is a cross-sectional view of an alternative embodiment of the proportioning valve body/proportioning valve nut interface.
Figure 6:
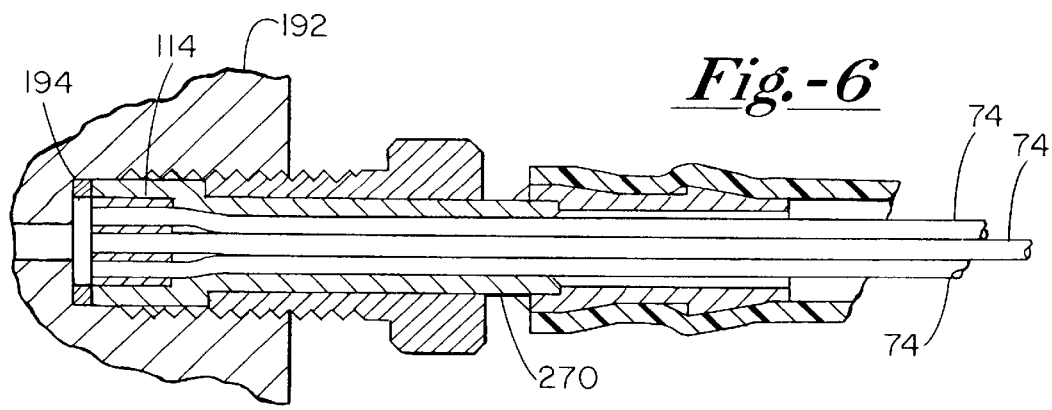
FIG. 6 is a cross-sectional view of an alternative embodiment of the proportioning valve body/proportioning valve nut interface.

Alternative embodiments for the degassing channel adjoining the proportioning valve body 192 are shown in FIGS. 4–6. In the embodiment illustrated in FIG. 4, proportioning valve nut 202 is similar to sealing nut 140 in the embodiment shown in FIGS. 2–3, wherein valve nut 202 preferably includes an exterior threaded portion 204 and a barbed portion 206 distal from the threaded portion. Valve nut 202 is hollow along its length, thereby providing an open channel 208 for receiving degassing tubes 74 therein. The wall of channel 208 serves as a portion of an outer boundary for the degassing chamber, which chamber is evacuated to remove gas that has permeated through the degassing tubes 74 from the mobile phase. Threaded portion 204 of valve nut 202 may be received in a female receptacle 190 in valve housing 192, which receptacle 190 is preferably cooperatively threaded. To seal interior portion 108, threaded portion 204 of valve nut 202 is inserted into female receptacle 190 such that threaded end 205 of valve nut 202 presses against a ferrule 114. Such pressure forms a gas-tight seal between the ferrule 114 and the valve nut 202. In a preferred embodiment of valve nut 202, at least a portion of threaded end 205 is recessed or angled inwardly such that as the threaded end 205 is forced against ferrule 114, the recessed or angled portion or threaded end 205 pushes the ferrule inwardly against degassing tubes 74. By pressing ferrule 114 inwardly while simultaneously pressing against the ferrule, the preferred end configuration forms an improved seal between threaded end 205 and ferrule 114.

Another alternative embodiment for a proportioning valve/degassing channel interface is shown in FIG. 5. Proportioning valve nut 250 is similar to proportioning valve nut 180 of FIGS. 2 and 3, in that valve nut 250 includes an exterior threaded portion 252 which threaded portion 252 may be received in a female receptacle 190 in proportioning valve body 192. Valve nut 250 contains a hollow channel 254 extending the length of valve nut 250. In the embodiment shown in FIG. 5, a flared liner tube 260 is disposed around degassing tubes 74, a portion of the liner tube 260 being positioned between valve nut 250 and degassing tubes 74 in hollow channel 254. Flared liner tube 260 is substantially cylindrical with one end being flared outwardly. Flared end 262 is positioned around degassing tubes 74 adjacent female receptacle end 110. As threaded portion 252 of valve nut 250 is inserted into female receptacle 190, threaded end 253 of valve nut 250 presses against flared end 262 of liner tube 260, thereby causing flared end 262 to press in against ferrule 114. Pressed ferrule 114 forms a vacuum seal between degassing tubes 74 and liner tube 260, and a liquid-tight seal between and around degassing tubes 74, and against ring spacer 194. Liner tube 260 is preferably fabricated from a rigid, strong material, for example stainless steel.

FIG. 6 illustrates an embodiment of the proportioning valve body/degassing channel interface wherein the liner tube 270 extends to ring spacer 194. As such, liner tube 270 completely contains ferrule 114 between the degassing tubes 74 and ring spacer 194, thereby sealing degassing tubes 74.

Figure 7:
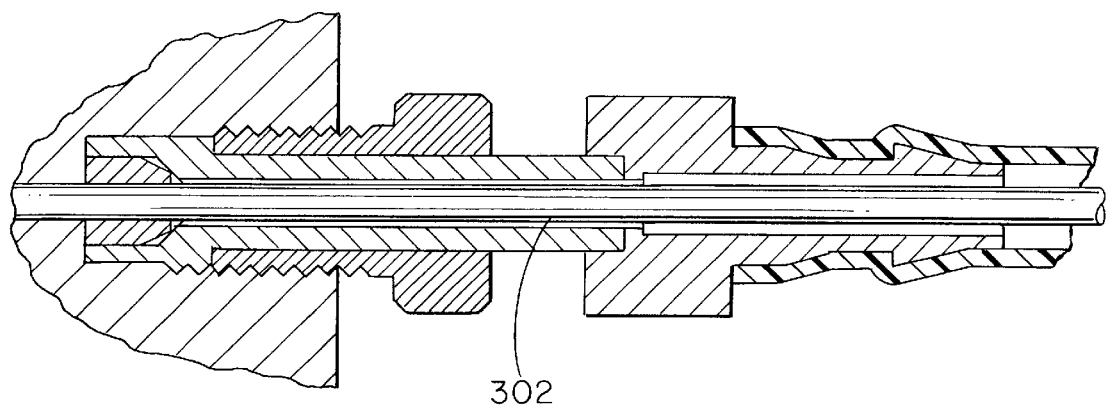
FIG. 7 is a cross-sectional view of an alternative embodiment of a degassing tube assembly having a single degassing tube.

Another preferred embodiment of the present invention is illustrated in FIG. 7. The embodiment shown in FIG. 7 includes a single degassing tube, as distinguished from the multiple-tube embodiments previously discussed. The single degassing-tube embodiment in FIG. 7 incorporates a similar configuration as the embodiment described with reference to FIG. 6. Single degassing tube 302 in FIG. 7 is substituted for degassing tubes 74 in FIGS. 2–6.

In some applications, a single degassing tube design is preferable over multiple degassing tube systems because the single degassing tube may utilize a larger inside diameter than the corresponding inside diameters of the multiple degassing tubes, thereby resulting in lower mobile phase flow restriction through the tube. Flow restriction is proportional to the length and inversely proportional to a fourth power function to inside diameter of tubing, so that a relatively shorter tube with a relatively larger inside diameter results in a relatively lower flow restriction. One method of reducing the flow restriction through the degassing tube is to divide a longer length of tubing into multiple shorter lengths of tubing, and distributing the total flow to each tube in parallel. Flow restriction could be further reduced, however, if the shorter length tubing is fabricated with a larger inside diameter while maintaining a constant total outer dimension, as in a single-tube system. Such a single degassing tube design is made possible through the use of highly gas-permeable materials such as Teflon AF. Such materials allow the degassing tubes to have a smaller overall inner surface area while maintaining a desired level of degassing performance. Since the overall surface area may be decreased, a significantly shorter single degassing tube with a larger inside diameter can be utilized.

Figure 8:
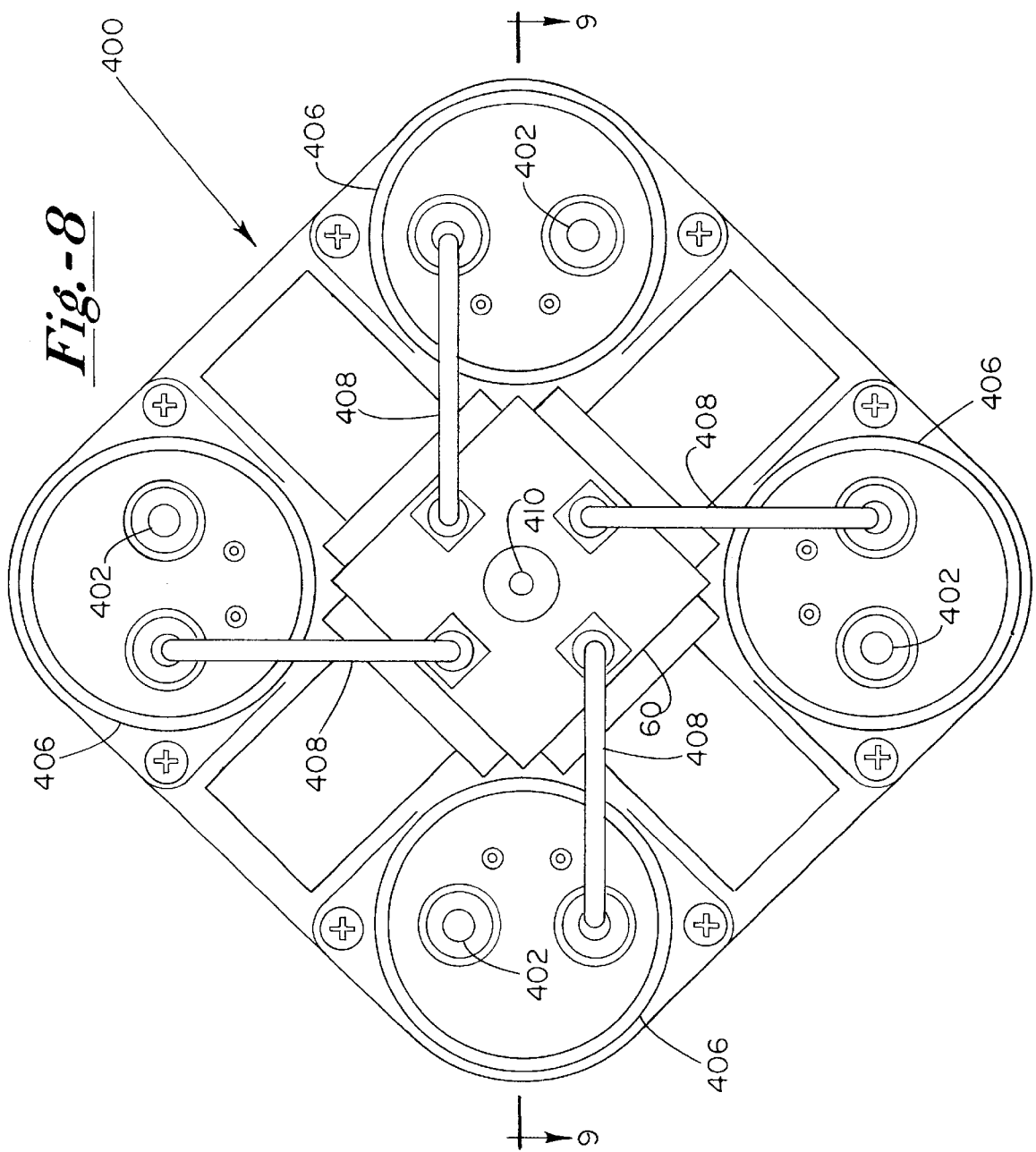
FIG. 8 is an end view of a proportioning valve body.
Figure 9:
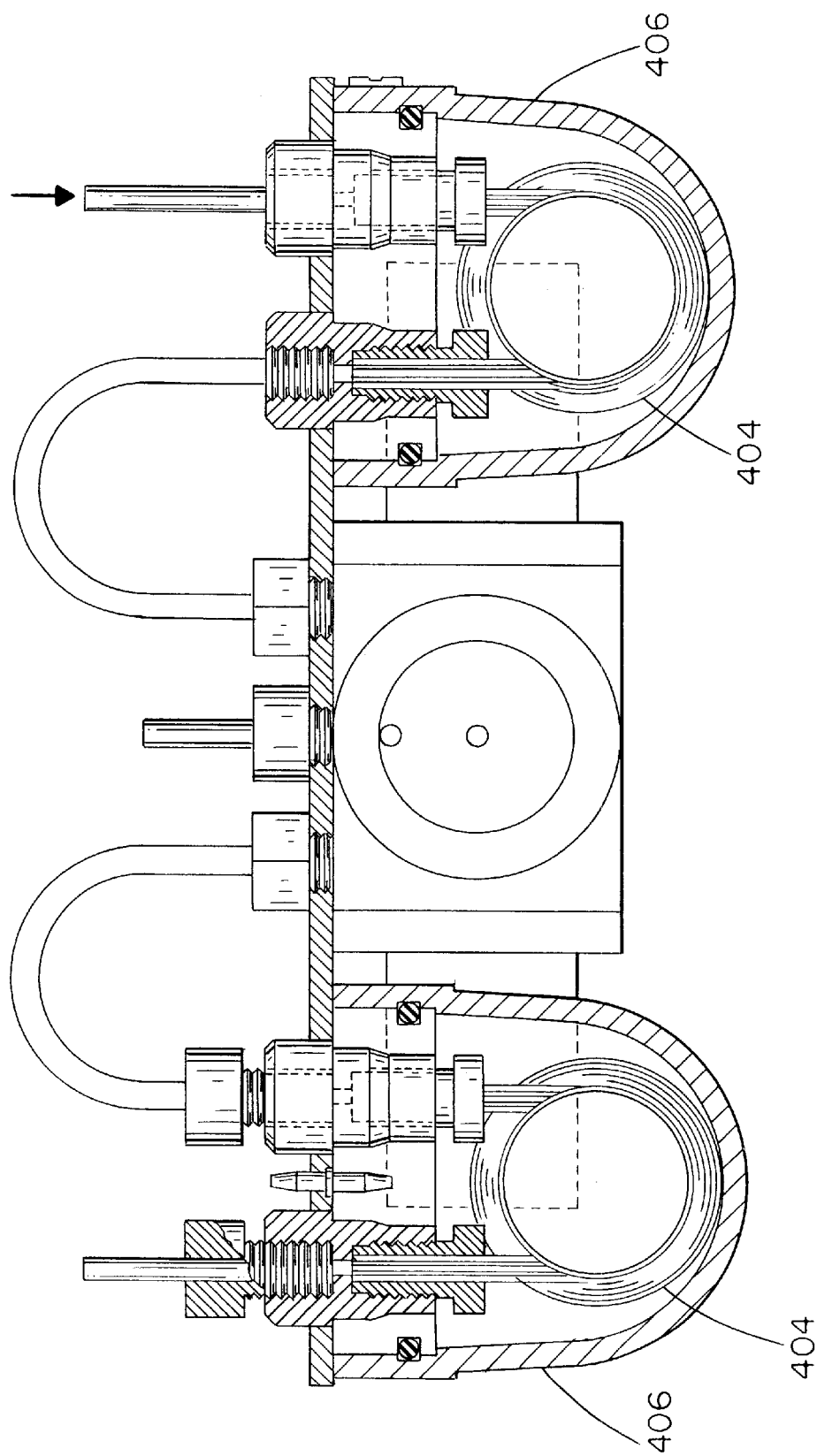
FIG. 9 is a cross-sectional cut view of a portion of the valve body illustrated in FIG. 8.

FIG. 8 illustrates a proportioning valve body 400 in accordance with the present invention. Incoming mobile phases flow into respective mobile phase inlets 402 in valve body 400. In some embodiments of the present invention, the mobile phases are then degassed in individual degassing coils 404, as shown in FIG. 9, which is a cut side view of FIG. 8. Degassing coils 404 are preferably disposed in individual vacuum chambers 406 so that permeated gas may be effectively removed. Degassing coils 404 are preferably coiled tubing fabricated from a gas-permeable material, most preferably Teflon AF 2400. Referring again to FIG. 8, the mobile phase is then passed to a blending chamber 60 through transfer tubes 408. Once in the blending chamber 60, a proportioning valve 62 comprising one or more solenoid valves blends the mobile phases into discrete mobile phase volumes of desired composition. This discrete blended volume of mobile phase then exits the proportioning valve body 400 through mobile phase outlet 410.

A preferred mode of implementing the present invention is as follows. As described above, one or more mobile phase streams are drawn from respective mobile phase reservoirs into mobile phase inlets 402 in proportioning valve body 400. The distinct mobile phase streams are then passed through a length of Teflon AF 2400 tubing in an individual vacuum chamber 406 to at least partially degas the mobile phases. The individual mobile phase streams are then passed to a proportioning valve 62, where the mobile phases are blended into discrete volumes of desired composition.

A mobile phase pump 80 draws the blended mobile phase into degassing channel 70 through mobile phase outlet 410. Once in the degassing channel 70, the mobile phase enters one or more degassing tubes 74, which are preferably Teflon AF 2400. The degassing tubes 74 are enclosed within a vacuum chamber 108 so that gas which permeates through degassing tubes 74 may be effectively removed from the degassing channel 70.

Degassing channel 70 may be coupled directly to mobile phase pump 80, or may be coupled to a transfer conduit 78 through a coupling union 90, as shown in FIGS. 1–3. In the embodiment illustrated in FIGS. 1–3, the mobile phase flows from the degassing tubes 74 into a transfer duct 130 in coupling union 90. From the coupling union 90, the mobile phase enters transfer conduit 78 for transportation to the mobile phase pump 80. The mobile phase pump 80 injects the mobile phase into a sample line, where a particular chemical sample to be analyzed is mixed with the mobile phase.

Figure 10:
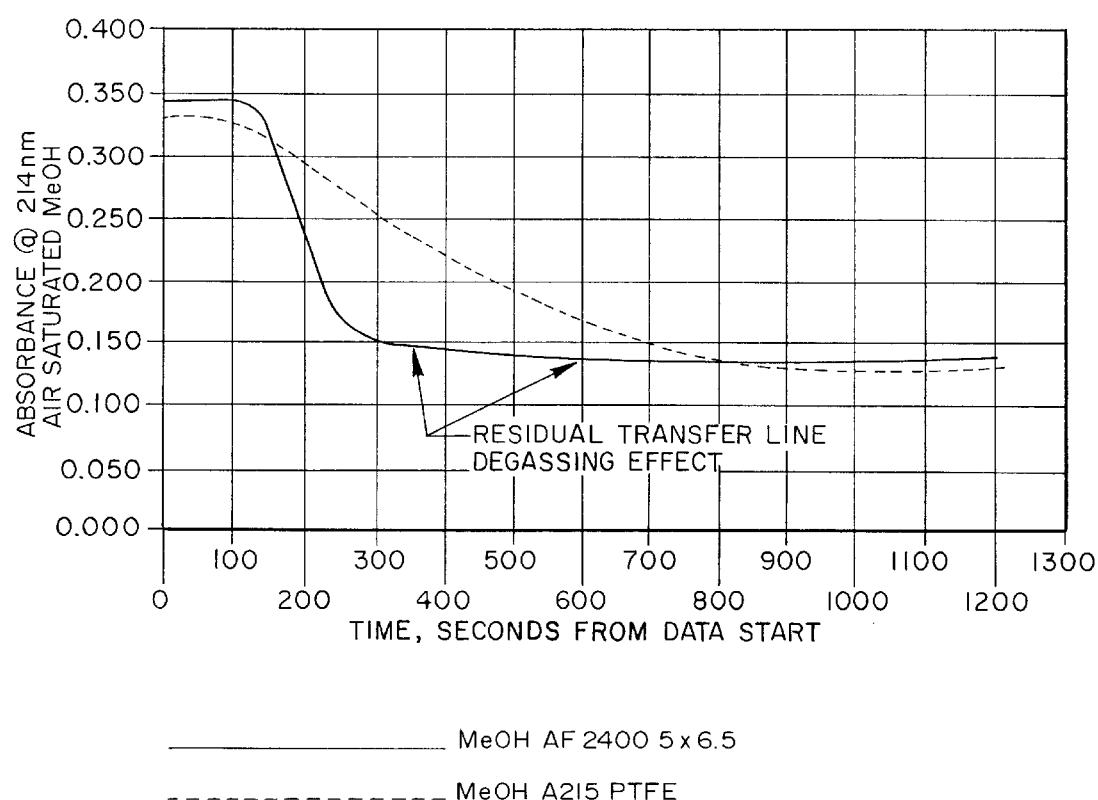
FIG. 10 is a graphical degassing efficiency comparison between PTFE and AF 2400 degassing tubing.

The above-described system has several advantages over known degassing systems. By utilizing an amorphous perfluorinated copolymer such as Teflon AF in the degassing tubes, a desired level of degassing may be accomplished in a shorter period of time, in a smaller degassing apparatus. The superior degassing efficiency of Teflon AF 2400 over a typical PTFE degassing tube material is shown in the graph in FIG. 10. Teflon AF 2400 degassing efficiency is represented by the solid line, while PTFE degassing efficiency is represented by the dashed line. As can be seen from the graph, light absorbance caused by oxygen in the mobile phase (methyl alcohol) is reduced to a nominal level more quickly in the Teflon AF 2400 tube than in the PTFE tube of similar degassing capacity. In fact, light absorbance is reduced to 15% in the AF 2400 tube in less than one half the time required in the PTFE tube. Due to the superior degassing capability of amorphous perfluorinated copolymers that was discovered by the present inventors, more compact degassing systems can be implemented while maintaining a desired level of degassing performance.

Another advantage of the present invention over known degassing systems is in the location of the degassing channel 70 in the liquid chromatography system. The degassing channel 70 of the present invention may be positioned downstream from the blending chamber 60, such that the degassing channel 70 receives discrete volumes of blended mobile phase. Due to flow characteristics in transfer lines between the proportioning valve and the mobile phase pump, significant mixing between the mobile phases typically occurs, resulting in the thermal and solubility effects which can cause the formation of gas bubbles in the mobile phase mix. This leads to inaccuracies in forming mixtures and gradients for chromatographic separations. When gas bubbles form in the transfer line, volumetric errors may result in formation of desired sample compositions due to the volume occupied by the gas bubbles. Placement of the degassing tube downstream from the mobile phase blending provides a means of removing such gas in the blended mobile phase.

A further advantage associated with the present invention is in degassing applications for an HPLC auto sampler. Mobile phase is used in an auto sampler system to wash the sample loop in preparation for the subsequent sample, to pre-fill the sample loop, and to dilute the sample to be measured. In auto sampler applications, degassed mobile phase will improve the dispensing and dilution accuracy of the auto sampler syringe, reduce impact on oxygen-sensitive samples, and minimize the potential for bubble formation as the result of "rapid fill" syringe cavitation. The present degassing technique may also be adapted to degas sample in the sample loop of an auto sampler. Such sample degassing preferably provides more consistent chromatographic measurements by reducing dissolved gas concentration in the analyzed material. In preferred embodiments, both the sample in the sample loop and the mobile phase are degassed using the technique of the present invention.

The invention has been described herein in considerable detail in order to comply with the Patent Statutes, and to provide those skilled in the art with the information needed to apply the novel principles and to construct and use embodiments of the invention as required. However, it is to be understood that the invention can be carried out by specifically different devices and that various modifications can be accomplished without departing from the scope of the invention itself.

What is claimed is:

1. A method of degassing one or more liquids in a flow-through vacuum apparatus comprising:
   a) providing one or more distinct mobile phases for transport in a gas-permeable, liquid-impermeable degassing tube, said degassing tube being at least partially disposed in a sealed conduit, which conduit is adapted to be connected to a vacuum source for evacuating the conduit;
   b) providing a pump means for drawing the one or more mobile phases through the degassing tube;
   c) providing a liquid blending means for mixing said one or more distinct mobile phases into a single blended mobile phase stream; and
   d) positioning said degassing tube downstream from said blending means, and between said blending means and said pump means.

2. A method as in claim 1, including blending multiple mobile phases into discrete volumes of desired composition before drawing the mobile phases into the degassing tube.

3. A method as in claim 1 wherein the degassing tube consists essentially of an amorphous perfluorinated copolymer.

4. A flow-through vacuum degassing apparatus comprising:
   a conduit forming a chamber and adapted to be connected to a vacuum source for creating a vacuum within the conduit;
   an inlet port forming an inlet connection and an outlet port forming an outlet connection for receiving and discharging a fluid to be degassed, said inlet connection and said outlet connection each including coupling means for fluidly interconnecting respective components in a liquid chromatography system; and
   a gas-permeable, liquid-impermeable tube for conducting the fluid through the conduit, said tube being operably connected between the inlet port and the outlet port for providing a degassing means disposed downstream from a fluid blending chamber component of said liquid chromatography system, which blending chamber operably mixes discrete fluids to form a chromatographic mobile phase.

5. A flow-through vacuum degassing apparatus as in claim 4 wherein said tube consists essentially of an amorphous perfluorinated copolymer.

6. A flow-through vacuum degassing apparatus as in claim 5 wherein said inlet and outlet connections comprise inverted ferrule couplings.

7. A flow-through vacuum degassing apparatus as in claim 6 wherein said inlet and outlet connections further comprise an interface grid disposed between a bulkhead fitting and a nut, the interface grid being formed of a polymeric material and having at least one bore adapted for adhesiveless sealing of the tube therethrough.

8. A flow-through vacuum degassing apparatus as in claim 4 wherein said tube is disposed between said blending chamber and a fluid pump.

9. A flow-through vacuum degassing apparatus as in claim 4 wherein said tube has multiple lumens.

10. A flow-through vacuum degassing apparatus as in claim 4 wherein said conduit is an elongate tube.

11. A flow-through vacuum degassing apparatus for use in degassing a liquid in a liquid chromatography system, comprising:
   a vacuum duct adapted to be connected to a source for creating a vacuum in the duct;
   a liquid inlet port and a liquid outlet port, said inlet port and said outlet port forming respective inlet and outlet connections, said inlet and outlet connections each including coupling means for interconnecting respective chromatographic components; and
   a degassing tube for conducting the liquid through the vacuum duct, said tube being connected to said inlet connection and said outlet connection, said tube being formed of a gas-permeable, liquid-impermeable material, said tube being operably disposed downstream from a liquid blending chamber so as to receive and degas multiple liquids blended together such that the blended liquid passing through the outlet port is suitably degassed for use as a mobile phase in said liquid chromatography system.

12. A flow-through vacuum degassing apparatus as in claim 11 wherein said tube consists essentially of an amorphous perfluorinated copolymer.

13. A flow-through vacuum degassing apparatus as in claim 12 wherein said inlet and outlet connections comprise inverted ferrule couplings.

14. A flow-through vacuum degassing apparatus as in claim 13 wherein said inlet and outlet connections further comprise an interface grid disposed between a bulkhead fitting and a nut, the interface grid being formed of a polymeric material and having at least one bore adapted for adhesiveless sealing of the tube therethrough.

15. A flow-through vacuum degassing apparatus as in claim 11 wherein said tube has a single lumen.

16. A flow-through vacuum degassing apparatus as in claim 11 wherein said tube has multiple lumens.

17. A flow-through vacuum degassing apparatus as in claim 11 wherein said conduit is an elongate tube.

18. A flow-through vacuum degassing apparatus as in claim 11 wherein said degassing tube is adopted for use as a sample loop in an HPLC auto sampler.

* * * * *